(12) United States Patent
Shukla

(10) Patent No.: US 11,059,015 B2
(45) Date of Patent: Jul. 13, 2021

(54) MICROCAPSULES MODIFIED WITH NANOMATERIAL FOR CONTROLLED RELEASE OF ACTIVE AGENT AND PROCESS FOR PREPARATION THEREOF

(71) Applicant: Council of Scientific and Industrial Research, New Delhi (IN)

(72) Inventor: Parshuram Gajanan Shukla, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 124 days.

(21) Appl. No.: 15/580,890

(22) PCT Filed: Jun. 8, 2016

(86) PCT No.: PCT/IN2016/050173
§ 371 (c)(1),
(2) Date: Dec. 8, 2017

(87) PCT Pub. No.: WO2016/199167
PCT Pub. Date: Dec. 15, 2016

(65) Prior Publication Data
US 2018/0161746 A1 Jun. 14, 2018

(30) Foreign Application Priority Data
Jun. 10, 2015 (IN) .......................... 1737/DEL/2015

(51) Int. Cl.
| | | |
|---|---|---|
| *B01J 13/18* | (2006.01) | |
| *B01J 13/20* | (2006.01) | |
| *C08L 39/06* | (2006.01) | |
| *A01N 25/28* | (2006.01) | |
| *A01N 25/18* | (2006.01) | |
| *A61K 9/50* | (2006.01) | |
| *C01B 32/158* | (2017.01) | |
| *C01B 32/198* | (2017.01) | |
| *A01N 43/60* | (2006.01) | |
| *B01J 31/02* | (2006.01) | |
| *C01B 33/40* | (2006.01) | |
| *C07C 69/80* | (2006.01) | |
| *C07C 211/09* | (2006.01) | |
| *C08L 75/02* | (2006.01) | |
| *C08L 75/04* | (2006.01) | |
| *C08L 77/00* | (2006.01) | |
| *C11B 9/00* | (2006.01) | |

(52) U.S. Cl.
CPC .............. *B01J 13/18* (2013.01); *A01N 25/18* (2013.01); *A01N 25/28* (2013.01); *A01N 43/60* (2013.01); *A61K 9/5031* (2013.01); *B01J 13/20* (2013.01); *B01J 31/0237* (2013.01); *C01B 32/158* (2017.08); *C01B 32/198* (2017.08); *C01B 33/40* (2013.01); *C07C 69/80* (2013.01); *C07C 211/09* (2013.01); *C08L 39/06* (2013.01); *C08L 75/02* (2013.01); *C08L 75/04* (2013.01); *C08L 77/00* (2013.01); *A61K 9/5005* (2013.01); *C01P 2004/64* (2013.01); *C08L 2207/53* (2013.01); *C11B 9/00* (2013.01)

(58) Field of Classification Search
CPC ........ A01N 25/18; A01N 25/28; A01N 43/60; A61K 9/5031; A61K 9/5005; B01J 13/18; B01J 13/20; B01J 31/0237; C01B 32/158; C01B 32/198; C01B 33/40; C07C 211/09; C07C 69/80; C08L 39/06; C08L 75/02; C08L 75/04; C08L 77/00; C08L 2207/53; C01P 2004/64
See application file for complete search history.

(56) References Cited

U.S. PATENT DOCUMENTS

| | | | |
|---|---|---|---|
| 6,864,217 B2 * | 3/2005 | Hacker .................. | A01N 43/76 504/128 |
| 2007/0003631 A1 | 1/2007 | Sayre et al. | |
| 2013/0109565 A1 | 5/2013 | Boday et al. | |
| 2014/0127309 A1 * | 5/2014 | Drake .................... | A01N 25/28 424/497 |
| 2016/0332131 A1 * | 11/2016 | Lee .......................... | B01J 13/06 |

FOREIGN PATENT DOCUMENTS

| | | |
|---|---|---|
| WO | 2008/009216 | 1/2008 |
| WO | 2010/131258 | 11/2010 |
| WO | 2012/166884 | 6/2012 |

OTHER PUBLICATIONS

Polymer Nanocomposites, From: Nanostructures, 2017.*
Polymer Nanocomposites by Arunkumar Lagashetty and A Venkataraman, Resosnace, Jul. 2015.*
Fereidoon et al., "Effect of nanoparticles on the morphology and thermal properties of self-healing poly(urea-formaldehyde) microcapsules," Journal of Polymer Research, vol. 20, No. 6, pp. 1-8, May 7, 2013.

(Continued)

*Primary Examiner* — Irina S Zemel
(74) *Attorney, Agent, or Firm* — Carmody Torrance Sandak & Hennessey LLP

(57) ABSTRACT

The present invention disclosed a microcapsule modified with nanomaterial for controlled release of active agent comprising; a core comprising active agent and said polymer shell encompassing said core; characterized in that said polymer shell is made up of polymer nanocomposite and a process for the preparation thereof.

25 Claims, 8 Drawing Sheets

(56) References Cited

OTHER PUBLICATIONS

Chuanjie et al., "Preparation and barrier properties of the microcapsules added nanoclays in the wall," Polymers for Advanced Technologies, vol. 20, No. 12, pp. 934-939, Dec. 1, 2009.
Yun et al., "pH and electro-responsive release behavior of MWCNT/PVA/PAAc composite microcapsules," Colliods and Surfaces A: Physicochemical and Engineering Aspects, vol. 368, No. 1-3, pp. 23-30, Sep. 20, 2010.

* cited by examiner

MICROCAPSULES MODIFIED WITH NANOMATERIAL FOR CONTROLLED RELEASE OF ACTIVE AGENT AND PROCESS FOR PREPARATION THEREOF

FIELD OF THE INVENTION

The present invention relates to a modified microcapsule for controlled release of active agent. More particularly, the present invention relates to a microcapsule modified with nanomaterial for controlled release of active agent and process for preparation of the same.

BACKGROUND AND PRIOR ART

Microcapsules (MICs) have drawn tremendous attention to the scientific community owing to their extensive applications in various fields such as agrochemicals, pharmaceuticals, electronic ink, coatings, catalysis, dyes, self healing materials and house hold products. MICs encompass the active or core materials by a polymeric wall and this active can be released during application by various release mechanism.

Many of such application need desired release pattern/rate of active agent from microcapsules. Release of active agent from microcapsules can take place via diffusion through capsule wall membrane, diffusion through any pores present in capsule wall, relaxation of polymer chains of capsule wall or by any environmental trigger like change in pH, temperature, ionic strength etc.

Release properties of capsules can be altered by varying the properties of capsule wall such as nature and composition of monomers, wall thickness and capsule size or by double encapsulation (capsule surface coating with another or same polymer). In many cases though these variations are tried there is no significant change in the release pattern/rate. There are ample reports describing polymer composites prepared with nano materials like nano-clay, graphene oxide and CNT (carbon nanotubes).

In the literature, various attempts have been made to overcome these problems including encapsulation of core materials by multi-layered capsule wall, decreasing the core loading and varying the properties of capsule wall such as nature and composition of monomer(s). Although, these variations have been tried to overcome the problems like leakage during storage and/or fast release, most attempts were resulted in no significant improvement in the release pattern.

In recent years, attempts on utilization of nanomaterials for the preparation of MICs have been increased significantly for several applications. However, majority of reports describe use of nanomaterials as a stabilizer for preparing Pickering emulsion prior to actual microencapsulation step or are adsorbed on microcapsule wall surface or used as core material. Although various strategies have been adopted to prepare MICs; these reports are scanty towards study of release profile of active from MICs. The nanoclays offer remarkable improvement in various properties including permeability with incorporation of small amount in polymer matrix. Therefore, research on polymer/clay nanocomposites has been focused towards establishment of structure property processing relationships between the polymer and nanoclays.

Article titled "Effect of nanoparticles on the morphology and thermal properties of self-healing poly(urea-formaldehyde) microcapsules" by A Fereidoon et al. published in *Journal of Polymer Research;* 2013, Vol. 20 Issue 6, p 1 reports self-healing microcapsules with improved morphology as well as thermal and water resistance were prepared by introducing either single-walled carbon nanotubes (SWCNTs) or aluminum oxide nanoparticles (nano-alumina) into a urea-formaldehyde resin (which acts as the wall material). However, the use of formaldehyde which is not accepted in most of the applications is the drawback of said microcapsules.

Article titled "Layer-by-layer deposition of clay and a polycation to control diffusive release from polyurea microcapsules" by J Hickey et al. published in *Journal of Membrane Science,* 2011, 369 (1-2), pp 68-76 reports polyurea microcapsules containing model organic fills were coated with clay and polycation layers to control diffusive release. This control process allows post-modification of the release rate without interfering with capsule formation. Clay layer on capsules causes 50% reduction in release rate. Method allows variation of release without interfering with capsule wall formation. However, the process is lengthy involving several steps for layer by layer deposition of nanoclay and polycation alternately.

Article titled "Controlled release study of phenol formaldehyde microcapsules containing neem oil as an insecticide" by A V Bagle et al. published in *International Journal of Polymeric Materials and Polymeric Biomaterials,* 2013, 62 (8), pp 421-425 reports a successful encapsulation of neem oil, one of the most effective biological insecticides, in phenol formaldehyde micro-capsules.

Article titled "Cross-linked multilayer composite films and microcapsules embedded carbon nanotubes" by Along Xiong et al. published in *Materials Letters,* 2013, Volume 105, pp 132-135 reports the layer-by-layer (LbL) assembly of multi-walled carbon nanotubes (MWCNTs) and poly (allylamine hydrochloride) (PAH) carried out via the electrostatic interactions on planar substrates and polystyrene (PS) microsphere templates. For the (PAH/MWCNTs)/PS core-shell microsphere composites upon cross-linking, the PS cores could be removed by dissolution and the stabilized PAH/MWCNTs shells transform to hollow microcapsules. The main drawback of this process is the process involves several steps.

Article titled "Preparation and barrier properties of the microcapsules added nanoclays in the wall" by F Chuanjie et al. published in *Polym. Adv. Technol,* 2009, 20, 934-939 reports poly(urea-formaldehyde) (PUF) microcapsules containing dicyclopentadiene (DCPD) prepared by in situ polymerization. For the preparation of UF/clay nanocomposite microcapsules, acid-modified montmorillonite (H-MMT) was used as an effective catalyst for the condensation of urea and formaldehyde, and the condensation polymerization in the galleries resulted in the delamination of the clay. However, drawbacks of this method are use of hydrochloric acid for modification of MMT and formaldehyde for preparation of MICs which increases environmental hazards and health problems. The use of formaldehyde as one of the MICs forming material is not accepted in many applications due to reasons as stated above PCT application no. 2015171429 discloses a nanocomposite microcapsule for self-healing of composites, said microcapsule comprising: a urea-formaldehyde shell having an outer surface; a liquid core comprising a polymerizable healing agent, said urea-formaldehyde shell encompassing said liquid core; and nanoparticulates, wherein at least a portion of said nanoparticulates are dispersed in said liquid core, and wherein at least a portion of said outer surface is covered by said nanoparticulates, wherein said nanoparticulates are selected from the group consisting of graphene nanoflakes, single and multiwall carbon nanotubes, carbon fibers/nanofibers, carbon black, nanoclay, nanotalc, boron nitride nanotubes, and boron nitride nanoflakes, and combinations thereof. The microcapsules reported here do not have wall made up of polymer nanocomposite but microcapsules contain core material wherein at least a portion of nano material is dispersed and at least a portion of outer surface of microcapsule shell is covered with nano material.

PCT application no. 2015126847 discloses a process for adjusting the wettability property of a plurality of on-demand activation-type microcapsules of a core and shell structure. The polymer matrix is selected from the group consisting of a polyurea, polyurethane, polyurea-urethane or a mixture thereof and the shell further comprises a plurality of particles in contact with the polymer matrix, and wherein the plurality of particles is a plurality of nanoclays.

US patent application no. 20110200658 disclosed a process for making microcapsules comprising i) forming a solution of a cross-linker in a liquid; ii) forming a slurry of a surface-modified particulate inorganic material in an aqueous medium; and iii) dispersing the solution of step i) in the slurry of step ii) and causing or allowing the cross-linker to react with the surface-modified particulate inorganic material so as to form a cross-linked microcapsule wall, wherein said particulate inorganic material is a mineral selected from kaolin, bentonite, alumina, limestone, bauxite, gypsum, magnesium carbonate, calcium carbonate, perlite, dolomite, diatomite, huntite, magnesite, boehmite, palygorskite, mica, vermiculite, hydrotalcite, hectorite, halloysite, gibbsite, kaolinite, montmorillonite, illite, attapulgite, laponite and sepiolite. This patent describes use of nanoclay to prepare non-crosslinked and crosslinked Pickering emulsion. Capsules obtained are termed as Pickering capsules.

Article titled "Preparation of polyurea microcapsules with different composition ratios: structures and thermal properties" by K Hong et al. published in *Materials Science and Engineering: A*, 1999, Volume 272, Issue 2, pp 418-421 reports polyurea microcapsules were prepared by emulsion polymerization after adding an aqueous solution of poly (vinyl alcohol) as protective colloid to an organic solution of migrin oil as the core substance with aliphatic isophorone diisocyanate (IPDI) and aromatic 2,4-toluene diisocyanate (TDI) as wall-forming materials.

In most of the microcapsules prepared by different micro-encapsulation methods porosity in the capsule wall/matrix is the main reason for observed leaky capsules and/or very fast release. For example in the formation of polyurea microcapsules wherein capsule wall is formed by the reaction of isocyanate either with amine or water using aqueous continuous phase, isocyanate react with water to produce carbon dioxide which creates the porosity during capsule wall formation. In other techniques like solvent evaporation or spray drying capsules wall/matrix is formed by evaporation of solvent causing creation of pores.

In order to avoid drawbacks of prior art microcapsules, there is a need for development of a microcapsule for controlled release of active agent. Accordingly, the inventors of the present invention provide a microcapsule modified with nanomaterial for controlled release of active agent.

OBJECTIVE OF INVENTION

The main objective of the present invention is to provide a microcapsule modified with nanomaterial for controlled release of active agent.

Another objective of the present invention is to provide a process for the preparation of microcapsules modified with nanomaterial in aqueous medium for controlled release of active agent.

SUMMARY OF THE INVENTION

Accordingly, the present invention provides a microcapsule modified with nanomaterial for controlled release of active agent comprising:
a) a polymer shell;
b) a core comprising active agent and said polymer shell encompassing said core;
characterized in that said polymer shell is made up of polymer nanocomposite.

In preferred embodiment, said active agent is water-insoluble and is selected from the group consisting of perfume, pharmaceutical, insect repellent, self-healing agent, flavouring agent, pesticide, enzyme, biocide, insect pheromone and industrial chemical reagent.

In another preferred embodiment, said active agent is selected from the group consisting of dimethyl phthalate, Jasmine oil and quinalphos.

In yet another preferred embodiment, wherein said polymer is selected from polyurea, polyurethane, polyester, polyamide and is prepared by in-situ polymerization such as polycondensation or polyaddition method during the process of making microcapsules.

In another embodiment, the present invention provides a process for the preparation of microcapsules modified with nanomaterial in aqueous medium comprising the steps of:
a) adding nanomaterial to the aqueous medium and sonicating to obtain the dispersed solution followed by addition of surfactant to the nanomaterial dispersed solution to afford reaction mixture;
b) adding a mixture of active agent and polyisocyanate to the reaction mixture of step (a) with constant stirring at temperature in the range of 25 to 30° C. to afford reaction mixture;
c) adding a solution of polyamine and catalyst diluted in surfactant solution to the reaction mixture of step (b) followed by stirring the mixture at temperature in the range of 25 to 50° C. for the period in the range of 3 to 24 hrs;
d) isolating the microcapsules by filtration of reaction mixture of step (c) followed by drying to afford microcapsules;
characterized in that said polymer shell is made up of polymer nanocomposite.

In preferred embodiment, said aqueous medium is water.

In another preferred embodiment, said polyisocyanate is selected from the group of aromatic polyisocyanate consisting of 2,4- and 2,6-toluene diisocyanate (TDI), naphthalene diisocyanate, diphenyl methane diisocyanate, triphenyl methane-p,p'p"-trityl triisocyanate, polymethylene polyphenylene isocyanate, 2,4,4'-diphenylether triisocyanate, 3,3'-dimethyl-4,4'-diphenyl diisocyanate, 3,3'-dimethoxy-4,4'diphenyl diisocyanate, triphenylmethane 4,4', 4" triisocyanate and the aliphatic polyisocyanate is selected from the group consisting of Dicyclohexylmethane 4,4'-diisocyanate, hexamethylene1,6-diisocyanate, isophorone diisocyanate (IPDI), trimethyl-hexamethylene diisocyanate, trimethylene diisocyanate, propylene-1,2-diisocyanate, butylene1,2-diisocyanate and mixtures thereof.

In yet another preferred embodiment, said polyamine is selected from the group consisting of polyaziridine such as Aziridine PZ-33, Aziridine PZ-28, Diethylenetriamine (DETA), Triethylenetetraamine (TETA), Tetraethylene Pentamine, 2,4,4'-Triaminodiphenylether, Bis(Hexamethylene) Triamine, Ethylene Diamine (EDA), Trimethylenedipiperidine (TMDP), Guanidine Carbonate (GUCA), Phenylene Diamine, Toluene Diamine, Pentamethylene Hexamine, 1,6-Hexamethylene Diamine, 2,4-Diamino-6-Methyl-1,3,5-Triazine, 1,2-Diaminocyclohexane, 4,4'-Diaminodiphenylmethane, 1,5-Diaminonaphthalene, Isophorone Diamine, Diamino Propane, Diaminobutane, Piperazine (PIP), Aminoethylenepiperazine (AEP), Tetraethylenepentamine (TEPA), poly (propylene glycol) bis (2-aminopropyl ether) or [Jeffamine D-230], and O,O'-bis(2-aminopropyl) polypropylene glycol-block-polyethylene glycol-block-poly propylene glycol [Jeffamine ED 600].

In still another preferred embodiment, said catalyst is selected from 4-Diazabicyclo (2, 2, 2) octane (DABCO), N,N'-dimethylaminoethanol, N,N'-dimethylcyclohexylamine, bis-(2-dimethylaminoethyl)ether, N,N'-dimethylacetylamine, diaminobicyclooctane, stannous octoate, dibutyltindilaurate and mixtures thereof.

In yet still another preferred embodiment, said surfactant is selected from the group consisting of polyvinylpyrrolidone (PVP), polyethylene glycol sorbitan monolaurate (tween 20), polyethylene glycol sorbitan monopalmitate (tween 40), polyethylene glycol sorbitan monooleate (tween 80), polyvinyl alcohol (PVA), poly(ethoxy)nonyl phenol, ethylene maleic anhydride (EMA) copolymer, Easy-Sperse (from ISP Technologies Inc.), sodium or potassium polyacrylate, sodium or potassium polymethacrylate, Brij-35, sodium lignosulphate, and mixtures thereof.

In yet still another preferred embodiment, said active agent is water-insoluble and is selected from the group consisting of perfume, pharmaceutical, insect repellent, self-healing agent, flavouring agent, pesticide, enzyme, biocide, insect pheromone and industrial chemical reagent.

In yet still another preferred embodiment, said nanomaterial is selected from graphene oxide, carbon nanofibers, carbon nanotubes such as multi-walled carbon nanotubes (MWCNT), modified multi-walled carbon nanotubes (MWCNT) and nanoclay such as Montmorillonite (MMT), Laponite, Hectorite, Saponite, Fluorohectorite, Fluoromica Kaolinite, Halloysite, and Cloisite $Na^+$.

DETAILED DESCRIPTION OF THE INVENTION

The invention will now be described in detail in connection with certain preferred and optional embodiments, so that various aspects thereof may be more fully understood and appreciated.

In the view of above, the present invention provides microcapsules modified with nanomaterial for controlled release of active agent comprising: a polymer shell made up of polymer nanocomposite; a core comprising active agent and said polymer shell encompassing said core and process for the preparation thereof.

In an embodiment, the present invention provides a microcapsule modified with nanomaterial for controlled release of active agent comprising:
  a) a polymer shell;
  b) a core comprising active agent and said polymer shell encompassing said core;
characterized in that said polymer shell is made up of polymer nanocomposite.

In preferred embodiment, said active agent is water-insoluble and is selected from the group consisting of perfume, pharmaceutical, insect repellent, self-healing agent, flavouring agent, pesticide, enzyme, biocide, insect pheromone and industrial chemical reagent.

In another preferred embodiment, said active agent is selected from the group consisting of dimethyl phthalate, Jasmine oil and quinalphos.

In yet another preferred embodiment, wherein said polymer is selected from polyurea, polyurethane, polyester, polyamide and is prepared by in-situ polymerization such as polycondensation or polyaddition method during the process of making microcapsules.

In another embodiment, said nanomaterial is selected from the group consisting of graphene oxide, carbon nanofibers, carbon nanotubes and nanoclay.

In preferred embodiment, said carbon nanotube is selected from multi-walled carbon nanotubes (MWCNT), modified multi-walled carbon nanotubes (MWCNT).

In another preferred embodiment, said nanoclay is selected from Montmorillonite (MMT), Laponite, Hectorite, Saponite, Fluorohectorite, Fluoromica Kaolinite, Halloysite, and Cloisite $Na^+$.

The present invention provides a process for the preparation of microcapsules containing water-insoluble active agent by in-situ polymerization in aqueous medium such that microcapsule wall is made up of polymer nanocomposite comprising either hydrophilic or hydrophobic, modified or unmodified nano-material such as nano-clay and carbon nanotubes.

Figure 1:
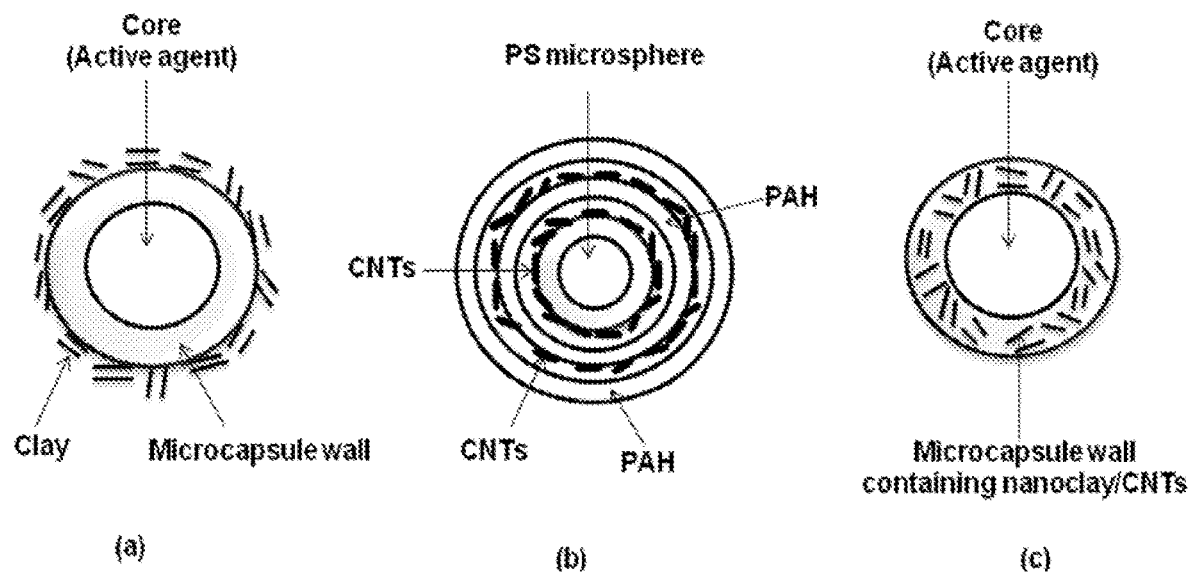
FIG. 1: Morphology of microcapsule/microspheres obtained by literature reports (a) and (b) and that described in the present invention (c)

In the prior art J. Hickey et al reported polyurea microcapsules containing model organic fills were coated with clay and polycation layers to control diffusive release and Along et al reported hollow microcapsules which are coated with MWCNT and poly (allylamine hydrochloride) (PAH) by layer by layer (LBL) deposition technique. The morphology of product reported by J. Hickey et al and that by Along et al shown in FIGS. 1(a) and 1(b) respectively are completely different from that reported in the present invention FIG. 1(c). The product described in the present invention is a microcapsule wherein the microcapsule wall is made up of polymer nanocomposite.

In another embodiment, the present invention provides a process for the preparation of microcapsules modified with nanomaterial in aqueous medium comprising the steps of:
a) adding nanomaterial to the aqueous medium and sonicating to obtain the dispersed solution followed by addition of surfactant to the nanomaterial dispersed solution to afford reaction mixture;
b) adding a mixture of active agent and polyisocyanate to the reaction mixture of step (a) with constant stirring at temperature in the range of 25 to 30° C. to afford reaction mixture;
c) adding a solution of polyamine and catalyst diluted in surfactant solution to the reaction mixture of step (b) followed by stirring the mixture at temperature in the range of 25 to 50° C. for the period in the range of 3 to 24 hrs;
d) isolating the microcapsules by filtration of reaction mixture of step (c) followed by drying to afford microcapsules;
characterized in that said polymer shell is made up of polymer nanocomposite.

In preferred embodiment, said aqueous medium is water.

In another preferred embodiment, said polyisocyanate is selected from aromatic polyisocyanates, aliphatic polyisocyanates and mixtures thereof.

Further the 'polyisocyanate' which can be used as microcapsule wall forming material include aromatic polyisocyanate is selected from the group consisting of 2,4- and 2,6-toluene diisocyanate (TDI), naphthalene diisocyanate, diphenyl methane diisocyanate, triphenyl methane-p,p'p"-trityl triisocyanate, polymethylene polyphenylene isocyanate, 2,4,4'-diphenylether triisocyanate, 3,3'-dimethyl-4,4'-diphenyl diisocyanate, 3,3'-dimethoxy-4,4'diphenyl diisocyanate, triphenylmethane 4,4', 4" triisocyanate, the aliphatic polyisocyanate is selected from the group consisting of Dicyclohexylmethane 4,4'-diisocyanate, hexamethylene1,6-diisocyanate, isophorone diisocyanate (IPDI), trimethyl-hexamethylene diisocyanate, trimethylene diisocyanate, propylene-1,2-diisocyanate, butylene1,2-diisocyanate and mixtures thereof.

In yet another preferred embodiment, said polyamine is selected from the group consisting of polyaziridine such as Aziridine PZ-33, Aziridine PZ-28, Diethylenetriamine (DETA), Triethylenetetraamine (TETA), Tetraethylene Pentamine, 2,4,4'-Triaminodiphenylether, Bis(Hexamethylene) Triamine, Ethylene Diamine (EDA), Trimethylenedipiperidine (TMDP), Guanidine Carbonate (GUCA), Phenylene Diamine, Toluene Diamine, Pentamethylene Hexamine, 1,6-Hexamethylene Diamine, 2,4-Diamino-6-Methyl-1,3,5-Triazine, 1,2-Diaminocyclohexane, 4,4'-Diaminodiphenylmethane, 1,5-Diaminonaphthalene, Isophorone Diamine, Diamino Propane, Diaminobutane, Piperazine (PIP), Aminoethylenepiperazine (AEP), Tetraethylenepentamine (TEPA), poly (propylene glycol) bis (2-aminopropyl ether) or [Jeffamine D-230], and O,O'-bis(2-aminopropyl) polypropylene glycol-block-polyethylene glycol-block-poly propylene glycol [Jeffamine ED 600].

In still another preferred embodiment, said catalyst is selected from 4-Diazabicyclo (2, 2, 2) octane (DABCO), N,N'-dimethylaminoethanol, N,N'-dimethylcyclohexylamine, bis-(2-dimethylaminoethyl)ether, N,N'-dimethyl-acetylamine, diaminobicyclooctane, stannous octoate, dibutyltindilaurate and mixtures thereof.

In yet still another preferred embodiment, said surfactant is selected from the group consisting of polyvinylpyrrolidone (PVP), polyethylene glycol sorbitan monolaurate (tween 20), polyethylene glycol sorbitan monopalmitate (tween 40), polyethylene glycol sorbitan monooleate (tween 80), polyvinyl alcohol (PVA), poly(ethoxy)nonyl phenol, ethylene maleic anhydride (EMA) copolymer, Easy-Sperse (from ISP Technologies Inc.), sodium or potassium polyacrylate, sodium or potassium polymethacrylate, Brij-35, sodium lignosulphate, and mixtures thereof.

Further, the surfactants are selected from but are not limited to acrylic acid-alkyl acrylate copolymer, poly (acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), poly(vinyl acetate-co-maleic anhydride), polyvinyl alcohols, polyalkylene glycols, polyoxyalkylene glycols and mixtures thereof.

In yet still another preferred embodiment, said active agent is water-insoluble and is selected from the group consisting of perfume, pharmaceutical, insect repellent, self-healing agent, flavouring agent, pesticide, enzyme, biocide, insect pheromone and industrial chemical reagent.

In another embodiment, said nanomaterial is selected from graphene oxide, carbon nanofibers, carbon nanotubes and nanoclay.

In preferred embodiment, said carbon nanotube is selected from multi-walled carbon nanotubes (MWCNT), modified multi-walled carbon nanotubes (MWCNT).

In another preferred embodiment, said nanoclay is selected from Montmorillonite (MMT), Laponite, Hectorite, Saponite, Fluorohectorite, Fluoromica Kaolinite, Halloysite, and Cloisite Na$^+$.

To have an understanding of change in porosity after addition of clay in microcapsule wall the neat MIC (Example 7) and MIC-Cloisite Na$^+$ (Example 8) samples by BET instrument. It is observed that incorporation of nanoclay in MICs results in significant reduction in porosity and pore dimension (Table 1).

TABLE 1

| Samples | Specific surface area (m$^2$/g) | Pore volume (cm$^3$/g) | Pore diameter (A°) |
| --- | --- | --- | --- |
| Neat MICs (Example 7) | 0.5167 | 0.1133 | 0.0877 |
| MIC-Cloisite Na+ (2 wt %) (Example 8) | 0.6136 | 0.06766 | 0.0411 |

The release rate constant (k) for the capsules of the present invention are in the range of 0.05 to 0.09 (min)$^{-n}$ and the order of release mechanism (n) is in the range of 0.15<n<0.19 as described by the equation given in example 15. It is to be noted that when n values are in close range (for example here 0.17±0.3) then only k values can be compared.

Figure 2:
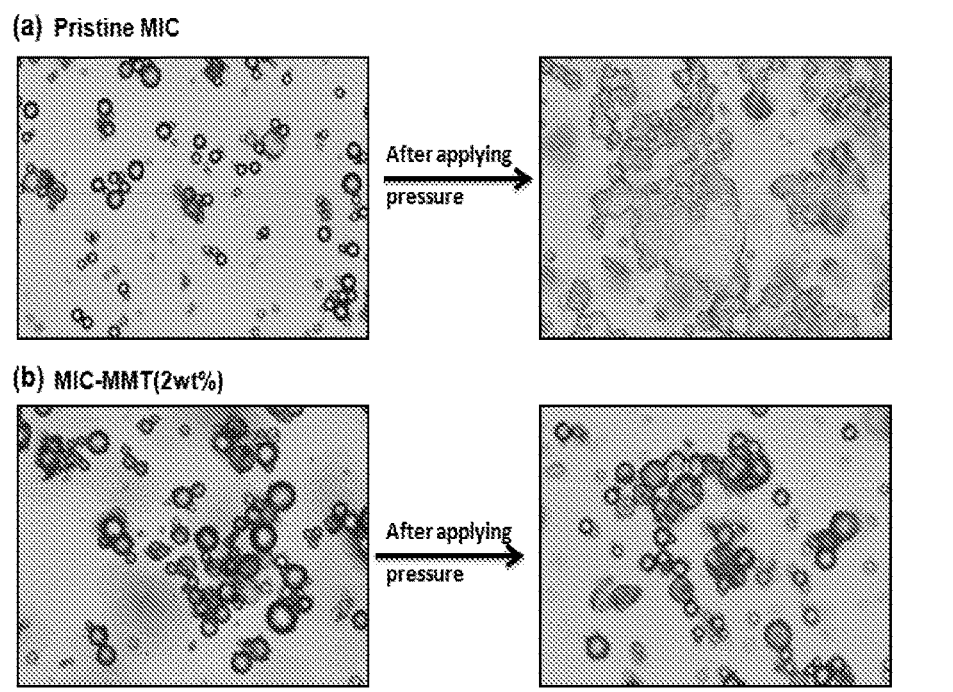
FIG. 2: Optical micrographs of pristine MICs (Example 1) and MIC-MMT (2 wt %) (Example 2) before and after applying pressure

The rupture behavior of pristine MICs (Example 1) and MIC-MMT (2 wt %) (Example 2) has been studied by optical microscopy. It is observed that most of the pristine MICs get ruptured (FIG. 2a) with pressure whereas most of the nanocomposite MICs remain intact and do not get ruptured (FIG. 2b). This experiment indicates that as expected with nanocomposite material, there is improvement in fracture strength of nanocomposite MICs as compared to pristine MICs.

Figure 3:
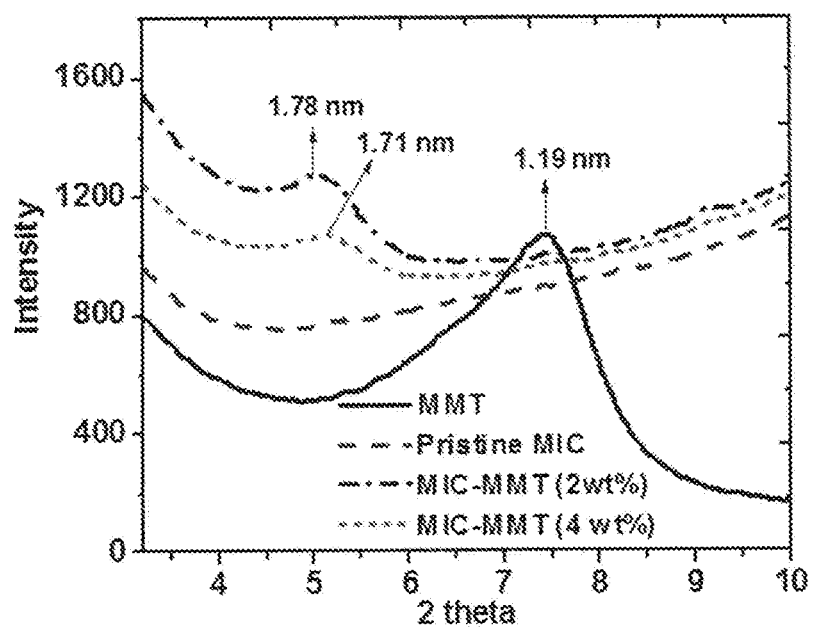
FIG. 3: XRD plots of MMT, pristine MICs (Example 1), MIC-MMT (2 wt %) (Example 2) and MIC-MMT (4 wt %) (Example 6)

FIG. 3 shows the XRD plots of MMT, pristine MICs (Example 1), MIC-MMT (2 wt %) (Example 2) and MIC-MMT (4 wt %) (Example 6). As expected pristine MICs show no 2θ peak indicating absence of MMT in MIC wall. The MMT shows 2θ peak at 7.42° with d-spacing of 1.19 nm. When MMT added to MICs, 2θ peak of MMT is shifted towards lower angle. MIC-MMT (2 wt %) and MIC-MMT (4 wt %) show 2θ peak at 4.99° and 5.14° with d-spacing of 1.78 nm and 1.71 nm, respectively. This observation indicates expansion of clay layers due to polyurea polymer chains and formation of polyurea/clay nanocomposites with intercalated structure.

Figure 4:
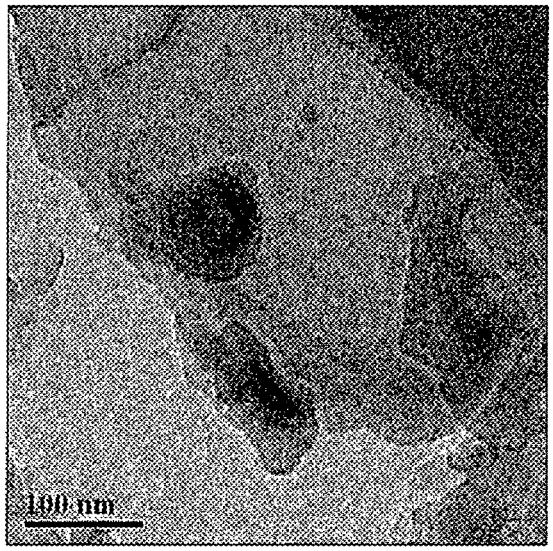
FIG. 4 TEM photographs of the pristine MICs (Example 1) [(a), (c)] and MIC-MMT (2 wt %) (Example 2) [(b), (d)] MICs at different locations.
Figure 4:
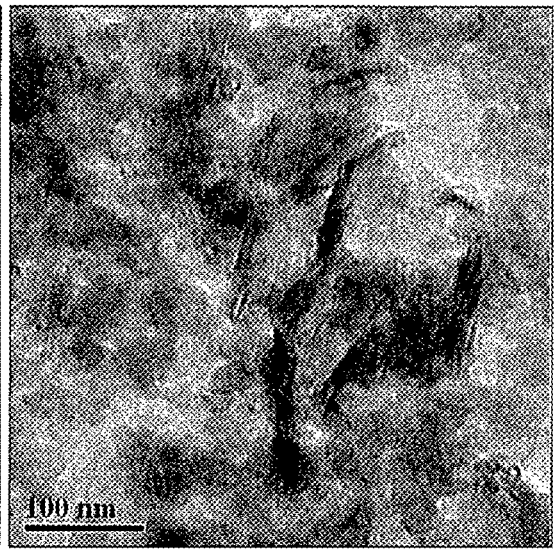
Figure 4:
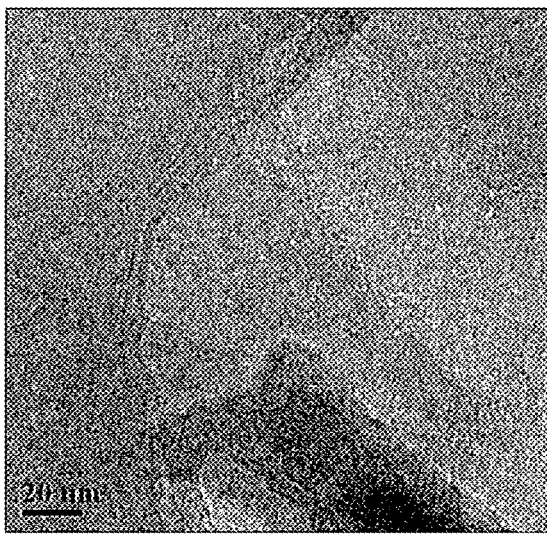
Figure 4:
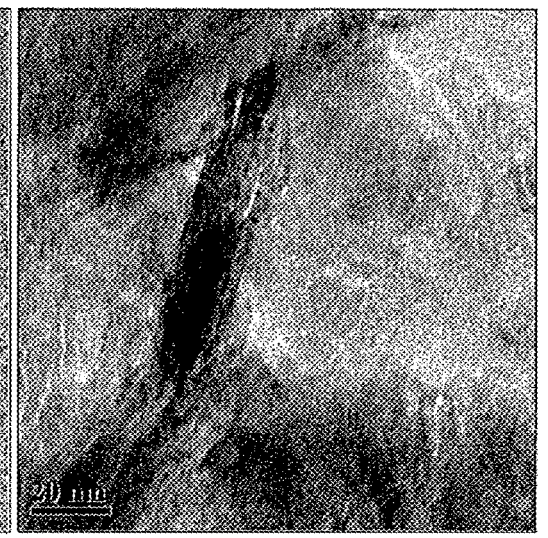

TEM photographs of pristine MICs (Example 1) and MIC-MMT (2 wt %) (Example 2) are presented in FIG. 4. The pristine MICs shows gray clouds of the polyurea matrix [FIGS. 4(a) and (c)]. On the other hand, MIC-MMT (2 wt %) [FIGS. 4(b) and (d)] exhibit nanoclay layers as dark lines. These layers are present throughout the photograph (FIG. 4d) and found separated by a fixed distance indicating the intercalated structure.

Figures 5, 5B:
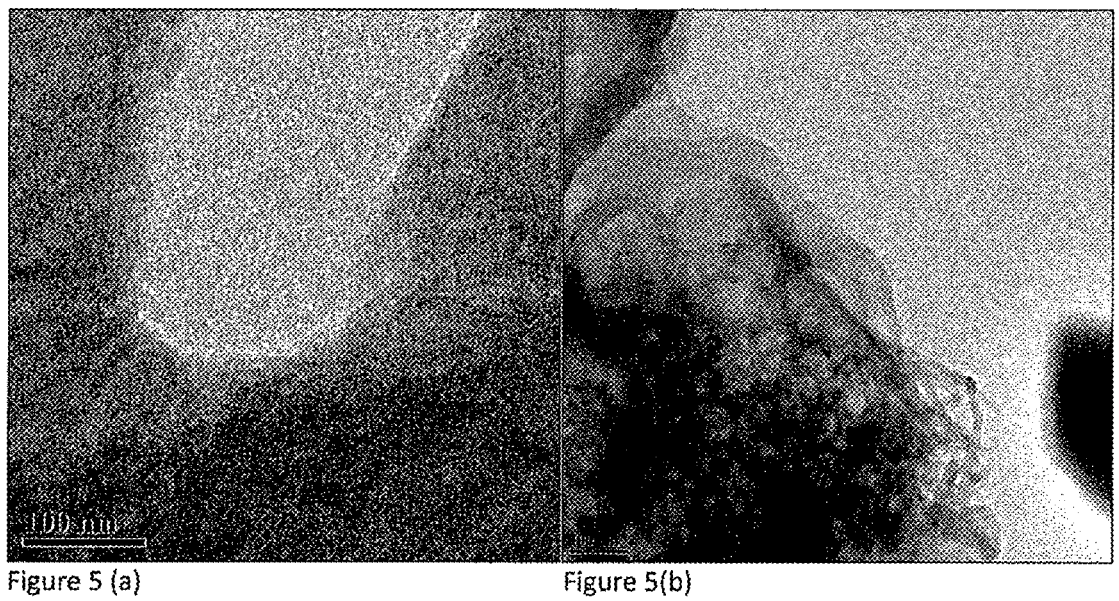
FIG. 5: TEM photographs of the pristine MICs (Example 1) [(a) and MIC-MWCNT 0.5% (Example 11)

TEM photographs of Example 1 and Example 11 are shown in FIG. 5. MICs of Example 1 prepared without addition of MWCNTs shows only gray cloud of the polyurea matrix (FIG. 5a) whereas TEM image of MICs of Example 11 clearly demonstrated the presence of embedded MWCNTs in the capsule wall (FIG. 5b).

The incorporation of nanoclay does not impart any change on surface morphology of MICs. SEM photographs of broken MICs shown in FIGS. 6(b), (c) and (d) indicate that prepared MICs are reservoir-type. It is well known that in most of the cases, MICs prepared by interfacial polymerization technique (IFP) have reservoir type structure. Smooth interior surface of MICs indicates that the presence of nanoclay in MIC wall does not affect the interior morphology of MICs as well.

The values of release rate constant (k) and types of release mechanism (n) are summarized in Table 2 below:

TABLE 2

| Samples | % Core loading by TGA | n | k (min) $^{-n}$ | $R^2$ |
|---|---|---|---|---|
| Pristine polyurea microcapsules (MIC) (Example 1) | 68 | 0.2920 | 0.0532 | 0.9834 |
| MIC with 1% MMT (Example 5) | 68 | 0.1817 | 0.0862 | 0.9735 |
| MIC with 2% MMT (Example 2) | 68 | 0.1780 | 0.0565 | 0.9330 |
| MIC with 4% MMT (Example 6) | 67 | 0.1538 | 0.0908 | 0.9890 |
| MIC with 2% Laponite (Example 4) | 69 | 0.1850 | 0.0572 | 0.9926 |
| Prior art MIC UF with 2% H-MMT (Example 3) | — | 0.1654 | 0.3253 | 0.8571 |

Value for n obtained in the present study for pristine MICs is 0.292 while all nanocomposite MICs show reduction in n values (0.17±0.015) indicating change in release mechanism. This is expected as with incorporation of nanoclay the polymer chains would have rigid nature resulting in different release mechanism. As the n values for all nanocomposite MICs (of present invention and those from comparative example 3) are same their release rate constant can be compared. It can be seen that release rate constant k values for all nanocomposite microcapsules of present invention are in the range of 0.05 to 0.09 $(min)^{-n}$ whereas k value for microcapsules of Example 3 (prior art) is much higher (k=0.325)

Figure 7:
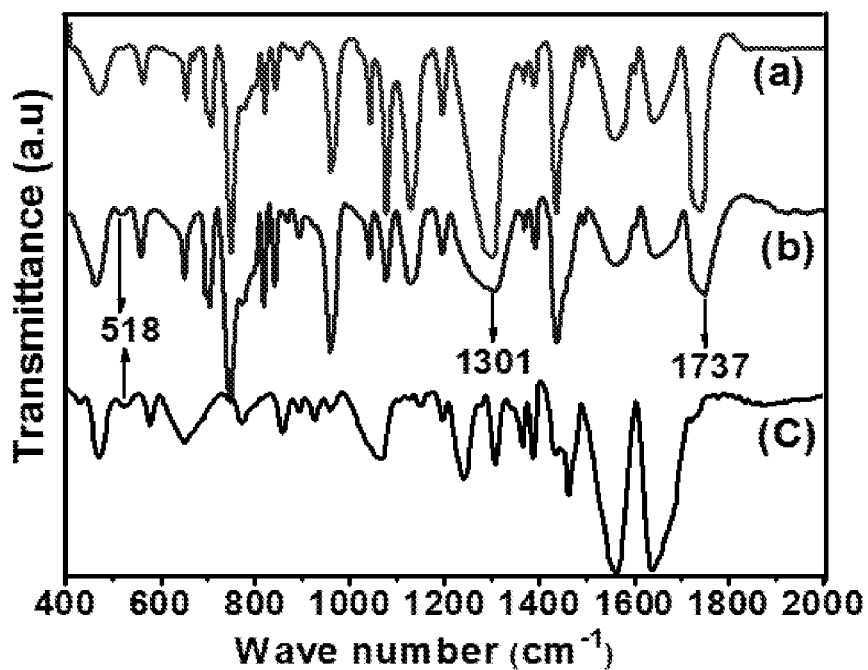
FIG. 7 FTIR spectra of (a) pristine MICs (Example 1), (b) MIC-MMT (2 wt %) (Example 2) and (c) MIS-MMT (2 wt %) (Example 14).

FIG. 7 shows FTIR spectra of the pristine MICs (Example 1), MIS-MMT (2 wt %) (Example 14) and MIC-MMT (2 wt %) (Example 2). FTIR spectra of MIS-MMT (2 wt %) and MIC-MMT (2 wt %) show a peak at 518 cm$^{-1}$ which corresponds to Al—O—Si deformation of nanoclay (FIGS. 7b and 7c). The peak at 518 cm$^{-1}$ is absent in the pristine MICs (FIG. 7a). This indicates that the presence of nanoclay in MIC-MMT (2 wt %) and formation of nanocomposites wherein clay layers are intercalated due to polyurea polymer which is also evidenced from XRD and TEM. The pristine MICs and MIC-MMT (2 wt %) exhibit strong peaks at 1737 cm$^{-1}$ and 1301 cm$^{-1}$ due to carbonyl (C=O) and ether (C—O—C) groups of DMP respectively. The same peaks are absent in the MIS-MMT (2 wt %).

Figure 8:
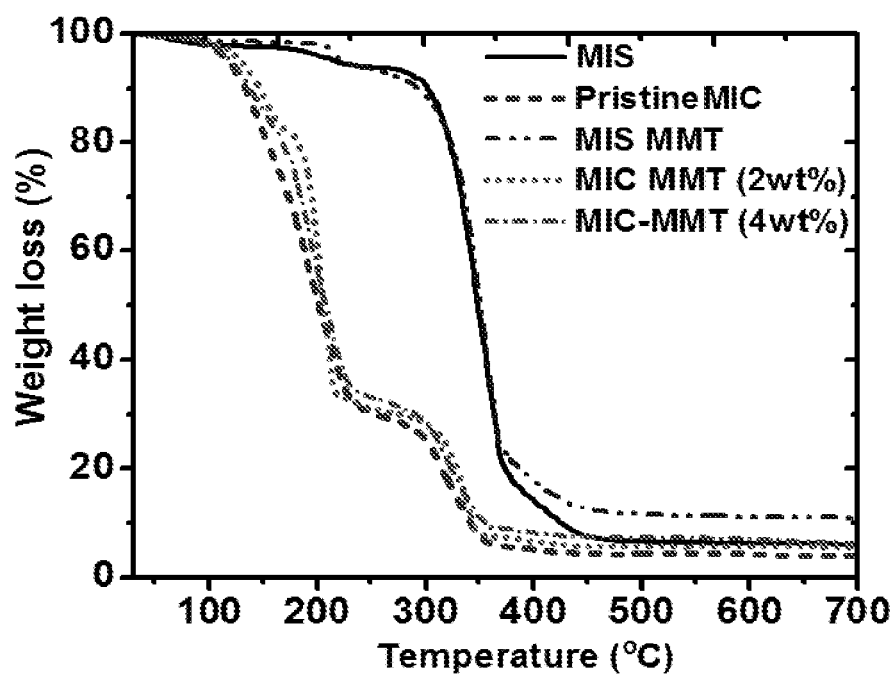
FIG. 8: TGA plots of Microsphere (MIS)(Example 13), pristine MICs (Example 1), Microsphere (MIS)-MMT (2 wt %) (Example 14), MIC-MMT (2 wt %) (Example 2) and MIC-MMT (4 wt %) (Example 6).

FIG. 8 shows TGA plots of the pristine MICs (Example 1), MIS (Example 13, MIS-MMT (2 wt %) (Example 14, MIC-MMT (2 wt %) (Example 2) and MIC-MMT (4 wt %) (Example 6). TGA thermograms of MIS and MIS-MMT (2 wt %) show onset of degradation around 290° C. Two steps degradation pattern was observed for all MICs. First degradation starts at about 120° C. owing to evaporation of the DMP, whereas second degradation starts at about 300° C. owing to the degradation of MIC wall. The loading (core content) of DMP obtained from TGA is tabulated in Table 2. The loading (%) of DMP in all MIC samples was found to be about 68±1% which is in good agreement with theoretical loading of DMP which is 70%. This result shows 96-98% encapsulation efficiency of MICs.

Figure 9:
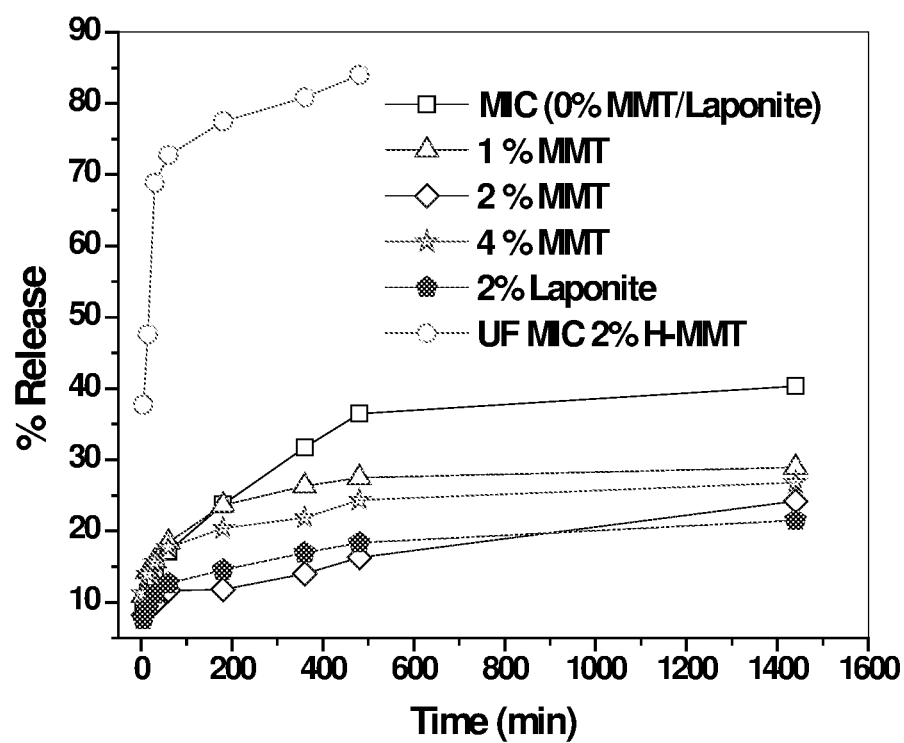
FIG. 9: Release profiles neat MICs (Example 1), nanocomposite MICs (Examples 2, 5, 6 for 2, 1 and 4 wt % MMT respectively), nanocomposite MICs (Example 4, 2 wt % Laponite) of the present invention and MICs prepared by reported method for comparison (Example 3)

FIG. 9 shows percentage (%) of DMP released in water from the pristine MICs and nanocomposite MICs with time. All nanocomposite MICs showed slower release of DMP as compared to the pristine MICs. This can be attributed to the facts that in formation of MICs the NCO group reacts with water resulting in formation of $CO_2$ which leads to porous polyurea wall. The presence of nanoclay in MIC wall would block these pores that are decrease in porosity is achieved (Table 1). This in turn reduces the permeability of DMP through MIC wall. The addition of 2 wt % of nanoclay in MICs resulted in significant reduction in the release rate of DMP as compared to pristine MICs.

Further, from FIG. 9 it is observed that the microcapsules (UF MIC 2% H-MMT) prepared as per the reported procedure from the prior art release active agent DMP is very fast. Within 100 mins prior art capsules show more than 70% release whereas capsules from the present invention show less than 25% release. From the present invention, capsules without nano-clay show faster release than those with nano-clay.

The following examples, which include preferred embodiments, will serve to illustrate the practice of this invention, it being understood that the particulars shown are by way of example and for purpose of illustrative discussion of preferred embodiments of the invention.

EXAMPLES

Example 1: Preparation of Polyurea Microcapsules (Pristine Microcapsules) Containing Dimethyl Phthalate (DMP) with 70% Loading 2 g of surfactant PVP (5% w.r.t continuous medium) was dissolved in 40 ml of distilled water in a 250 ml beaker. To this surfactant solution, mixture of 5 g of DMP and 1.7 g of IPDI was added while stirring the mixture at 1000 rpm (revolutions per minute) using turbine type stirrer at 27° C. Then mixture of 0.45 g of EDA and 0.04 g of DABCO was diluted in 15 g of 5% PVP solution and added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-60 microns and majority of capsules were 10-30 microns. The yield of microcapsules obtained was 65%.

Example 2: Preparation of Polyurea/MMT Microcapsules Containing Dimethyl Phthalate (DMP) with 70% Loading (2 wt % MMT, w.r.t Total Microcapsule Weight)

0.14 g of MMT was added to 40 ml of distilled water in a 250 ml beaker and sonicated for 30 minutes. 2 g of surfactant PVP was then added to the nanoclay dispersed solution and sonication continued for further 30 minutes. Then mixture of 5 g of DMP and 1.7 g of IPDI was added while stirring the mixture at 1000 rpm (revolutions per minute) using turbine type stirrer at 27° C. Then mixture of 0.45 g of EDA and 0.04 g of DABCO was diluted in 15 g of 5% PVP solution and added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-50 microns and majority of capsules were 5-25 microns. The yield of microcapsules obtained was 86%.

Example 3: Prior Art UF Microcapsules for Comparison a) Preparation of H-MMT:
0.3 g of Na-MMT was added to 15 ml of 1 mol/Lit HCl in a three-necked flask, and stirred vigorously for 12 hours at 80° C. The clay was filtered and washed with distilled water repeatedly up to pH 7 until no chloride was detected with a drop of 0.1 mol/l AgNO3 solution. Then the protonated clay was air-dried for two days.
b) Preparation of UF Microcapsules Containing Dimethyl Phthalate (DMP) with 70% Loading:
0.2 g of SDS (sodium dodecyl sulphate) was mixed with 100 ml deionized water in a 250 ml beaker and stirred at 500 rpm (revolutions per minute) using turbine type stirrer. Under agitation, 2.5 g urea, 0.25 g ammonium chloride and 0.25 g resorcinol were added one by one to the solution and the temperature of the mixture was maintained at 24° C. Then, the pH was adjusted to 3.5 by using NaOH and HCl. 9.3 g of DMP was added drop by drop to form an emulsion and allowed to stabilize for 10 min. After stabilization, 6.3 g of 37 wt % aqueous solution of formaldehyde mixed with 0.29 g H-MMT (with an ultrasonic pre-treatment) was added to the emulsion. The mixture was heated at the rate of 1° C./min to the target temperature of 55° C. After 3 hours, the reaction was ended. The microcapsules were isolated by filtration using deionized water and air-dried for 12 hours.

Example 4: Preparation of Polyurea/Laponite Microcapsules Containing Dimethyl Phthalate (DMP) with 70% Loading, (2 wt % Laponite w.r.t Total Microcapsule Weight)

0.14 g of Laponite was added to 40 ml of distilled water in a 250 ml beaker and sonicated for 30 minutes. 2 g of surfactant PVP was then added to the nanoclay dispersed solution and sonication continued for further 30 minutes. Then mixture of 5 g of DMP and 1.7 g of IPDI was added while stirring the mixture at 1000 rpm (revolutions per minute) using turbine type stirrer at 27° C. Then mixture of 0.45 g of EDA and 0.04 g of DABCO was diluted in 15 g of 5% PVP solution and added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-50 microns and majority of capsules were 5-25 microns. The yield of microcapsules obtained was 78%.

Example 5: Preparation of Polyurea/MMT Microcapsules Containing Dimethyl Phthalate (DMP) with 70% Loading (1 wt % MMT w.r.t Total Microcapsule Weight)

0.07 g of MMT was added to 40 ml of distilled water a 250 ml beaker and sonicated for 30 minutes. 2 g of surfactant PVP was then added to the nanoclay dispersed solution and sonication continued for further 30 minutes. Then mixture of 5 g of DMP and 1.7 g of IPDI was added while stirring the mixture at 1000 rpm (revolutions per minute) using turbine type stirrer at 27° C. Then mixture of 0.45 g of EDA and 0.04 g of DABCO was diluted in 15 g of 5% PVP solution and added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-50 microns and majority of capsules were 5-25 microns. The yield of microcapsules obtained was 76%.

Example 6: Preparation of Polyurea/MMT Microcapsules Containing Dimethyl Phthalate (DMP) with 70% Loading (4 wt % MMT w.r.t Total Microcapsule Weight)

0.28 g of MMT was added to 40 ml of distilled water a 250 ml beaker and sonicated for 30 minutes. 2 g of surfactant PVP was then added to the nanoclay dispersed solution and sonication continued for further 30 minutes. Then mixture of 5 g of DMP and 1.7 g of IPDI was added while stirring the mixture at 1000 rpm (revolutions per minute) using turbine type stirrer at 27° C. Then mixture of 0.45 g of EDA and 0.04 g of DABCO was diluted in 15 g of 5% PVP solution and added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-50 microns and majority of capsules were 5-25 microns. The yield of microcapsules obtained was 75%.

Example 7: Preparation Polyurea Microcapsules Containing Dimethyl Phthalate (DMP) with 50% Loading 2.5 g of surfactant PVP (5% w.r.t continuous medium) was dissolved in 50 g of distilled water in a 250 ml beaker. To the surfactant solution, mixture of 5 g of DMP and 2.5 g of TDI was added while stirring the mixture at 1000 rpm (revolutions per minute) using turbine type stirrer at 50° C. After completion of 1 hour, mixture of 2.5 g TDI in 25 gm of PVP (5%) solution was added into the reaction mixture. The reaction mixture was stirred for 3.5 hours at 50° C. followed by the addition of 0.3 gm of fumed silica. Then temperature and stirring speed was reduced to 35° C. and 500 rpm, respectively. Thereafter the mixture was stirred for further 1 hour and 100 ml distilled water was added. The microcapsules thus formed were centrifuged at 8000 rpm for 15 minutes followed by addition of 0.11 g, 0.23 g, and 0.21 g fumed silica at regular interval. The microcapsules thus formed were isolated by filtration and washed with distilled water and oven dried at 50° C. for 10 hours. The microcapsules found to have the size range of 2-70 microns and majority of capsules were 5-40 microns. The yield of microcapsules obtained was 76%

Example 8: Preparation of Polyurea/Cloisite $Na^+$ Microcapsules Containing Dimethyl Phthalate (DMP) with 50% Loading (2 wt % Cloisite $Na^+$ w.r.t Total Microcapsule Weight)

0.2 g of Cloisite $Na^+$ was added in 10 g of PVP (5%) solution in 100 ml beaker and sonicated for 45 minutes. Parallelly, 2.5 g of surfactant PVP (5% w.r.t continuous medium) was dissolved in 50 g of distilled water in a 250 ml beaker. To the surfactant solution, mixture of 5 g of DMP and 2.5 g of TDI was added while stirring the mixture at 1000 rpm (revolutions per minute) using turbine type stirrer at 50° C. After completion of 1 hour, mixture of 2.5 g TDI in 25 gm of PVP (5%) solution was added into the reaction mixture. The reaction mixture was stirred for 3.5 hours at 50° C. followed by the addition of 0.3 gm of fumed silica. Then temperature and stirring speed was reduced to 35° C. and 500 rpm, respectively. Thereafter the mixture was stirred for further 1 hour and 100 ml distilled water was added. The microcapsules thus formed were centrifuged at 8000 rpm for 15 minutes followed by addition of 0.11 g, 0.23 g, and 0.21 g fumed silica at regular interval. The microcapsules thus formed were isolated by filtration and washed with distilled water and oven dried at 50° C. for 10 hours. The microcapsules found to have the size range of 2-70 microns and majority of capsules were 5-40 microns. The yield of microcapsules obtained was 63%.

Example 9: Preparation of Polyurea Microcapsules Containing Jasmine (Jasmine Absolute) with 50% Loading (Cloisite $Na^+$, 2 wt % w.r.t Total Content)

1.25 g of surfactant PVP K90 (5 wt % w.r.t continuous medium) was dissolved in 25 g of distilled water in 250 mL beaker by sonicating the mixture for 30 minutes. To this solution, 0.078 g Cloisite $Na^+$ (2 wt % w.r.t. total microcapsules weight) was added and sonicated for further 30 minutes. Then mixture of 1.95 g of jasmine and 1.45 g TDI was added into the clay-surfactant dispersion while stirring the mixture at 1000 rpm (revolutions per minute) using turbine type stirrer at 27° C. Then 0.5 g of EDA was dissolved in 3 g of distilled water and added drop wise at the rate of 0.3-0.6 g of EDA solution per minute. After 10 min, 10 g of 5 wt % PVP K90 solution was added. The reaction mixture was stirred for 3 hours at room temperature and 2 hours at 50° C. Then the reaction temperature was brought to room temperature and stirring speed was reduced to 500 rpm. Thereafter, the mixture was stirred for further 17 hours. The microcapsules thus formed were isolated by filtration and washed with distilled water and dried at room temperature. The microcapsules found to have the size range of 20-200 microns and majority of capsules were 25-100 microns. The yield of microcapsules obtained was 69%.

Example 10: Preparation of Polyurea Microcapsules Containing Quinalphos with 50% Loading (Cloisite $Na^+$, 2 wt % w.r.t Total Content)

1.25 g of surfactant PVP K90 (5 wt % w.r.t continuous medium) was dissolved in 25 g of distilled water in 250 mL beaker by sonicating the mixture for 30 minutes. To this solution, 0.078 g Cloisite $Na^+$ (2 wt % w.r.t. total microcapsules weight) was added and sonicated for further 30 minutes. Then mixture of 1.95 g of quinalphos and 1.45 g TDI was added into the clay-surfactant dispersion while stirring the mixture at 1000 rpm (revolutions per minute) using turbine type stirrer at 27° C. Then 0.5 g of EDA was dissolved in 3 g of distilled water and added drop wise at the rate of 0.3-0.6 g of EDA solution per minute. The reaction mixture was stirred for 3 hours at room temperature and 2 hours at 50° C. Then the reaction temperature was brought to room temperature and stirring speed was reduced to 500 rpm. Thereafter, the mixture was stirred for further 17 hours. The microcapsules thus formed were centrifuged at 8000 rpm and stored as dispersion in distilled water. The microcapsules found to have the size range of 10-200 microns and majority of capsules were 20-50 microns.

Example 11: Preparation of Polyurea/Modified MWCNT Microcapsules Containing Dimethyl Phthalate (DMP) with 70% Loading (0.5 wt % NCO Modified MWCNT w.r.t Total Microcapsule Weight)

a) Modification of MWCNT by IPDI:
0.1 g of MWCNT-COOH (carboxylic acid modified MWCNTs) was taken in 100 ml three-neck round bottom flask containing 10 mg (1 wt %) of dibutyltin diluarate (DBTDL) as catalyst and 20 ml of acetone. To this mixture, 30 ml (excess) of IPDI was added and the suspension was heated at 50° C. for 7 hours under constant stirring and $N_2$ atmosphere. After cooling to 27° C., the reaction mixture was filtered and sonicated in acetone for 1 hour and washed with acetone at least three times to remove unreacted IPDI molecule. The obtained IPDI modified MWCNTs were dried in vacuum oven at 70 C for 12 hours.

b) Microcapsule Preparation:
0.035 g of modified MWCNT (MWCNT-NHRNCO) was added to 40 ml of distilled water in distilled water and sonicated for 30 minutes. 2 g of surfactant PVP was then added to the MWCNTs dispersed solution and sonication continued for further 30 minutes. To this mixture 5 g of DMP and 1.7 g of IPDI was added while stirring the mixture at 1000 rpm (revolutions per minute) using turbine type stirrer at 27° C. Then the mixture of 1 g of EDA and 0.04 g of DABCO was diluted in 15 g of 5% PVP solution and then added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-50 microns and majority of capsules were 5-25 microns. The yield of microcapsules obtained was 72%.

Example 12: Preparation of Polyurea/Unmodified MWCNT Microcapsules Containing Dimethyl Phthalate (DMP) with 70% Loading (0.5 wt % Unmodified MWCNT w.r.t Total Microcapsule Weight)

0.035 g of MWCNT (unmodified) was added to 40 ml of distilled water in distilled water and sonicated for 30 minutes. 2 g of surfactant PVP was then added to the MWCNTs dispersed solution and sonication continued for further 30 minutes. To this mixture 5 g of DMP and 1.7 g of IPDI was added while stirring the mixture at 1000 rpm (revolutions per minute) using turbine type stirrer at 27° C. Then the mixture of 1 g of EDA and 0.04 g of DABCO was diluted in 15 g of 5% PVP solution and then added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-50 microns and majority of capsules were 5-25 microns. The yield of microcapsules obtained was 72%.

Example 13: Preparation of Blank Polyurea Microspheres (MIS)

2 g of surfactant PVP (5% w.r.t continuous medium) was dissolved in 40 ml of distilled water in a 250 ml beaker. To this surfactant solution, 1.7 g of IPDI was added while stirring the mixture at 1000 rpm (revolutions per minute) using turbine type stirrer at 27° C. Then mixture of 0.45 g of EDA and 0.04 g of DABCO was diluted in 15 g of 5% PVP solution and added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The yield of microcapsules obtained was 40%.

Example 14: Preparation of Blank Polyurea/MMT Microspheres (MIS) with 2 wt % of MMT 0.14 g of MMT was added to 40 ml of distilled water in a 250 ml beaker and sonicated for 30 minutes. 2 g of surfactant PVP was then added to the nanoclay dispersed solution and sonication continued for further 30 minutes. Then 1.7 g of IPDI was added while stirring the mixture at 1000 rpm (revolutions per minute) using turbine type stirrer at 27° C. Then mixture of 0.45 g of EDA and 0.04 g of DABCO was diluted in 15 g of 5% PVP solution and added drop wise at the rate of 0.7-1 g of EDA solution per minute. The reaction mixture was stirred at 27° C. for 5 hours and at 50° C. for 1 hour. Then 0.2 g of fumed silica was added and the stirring was continued for further 30 minutes at 500 rpm. The microcapsules thus formed were isolated by filtration and washed with distilled water and dried in oven at 70° C. for 8 hours. The microcapsules found to have the size range of 2-50 microns and majority of capsules were 5-25 microns. The yield of microcapsules obtained was 63%.

Example 15: Characterization of Microcapsules a) Rupture Behavior:

Olympus BX-60, USA optical microscope fitted with Olympus SC30 digital camera was used to measure the size of MICs and to observe the ruptured MICs. To get an idea about fracture strength of MICs a simple method was explored. Small quantity of MICs was taken on a glass slide and covered with glass coverslip. This coverslip was gently pressed with finger. Optical microscopic images of pristine MICs and nanocomposite MICs were captured before and after applying the pressure.

Figure 6:
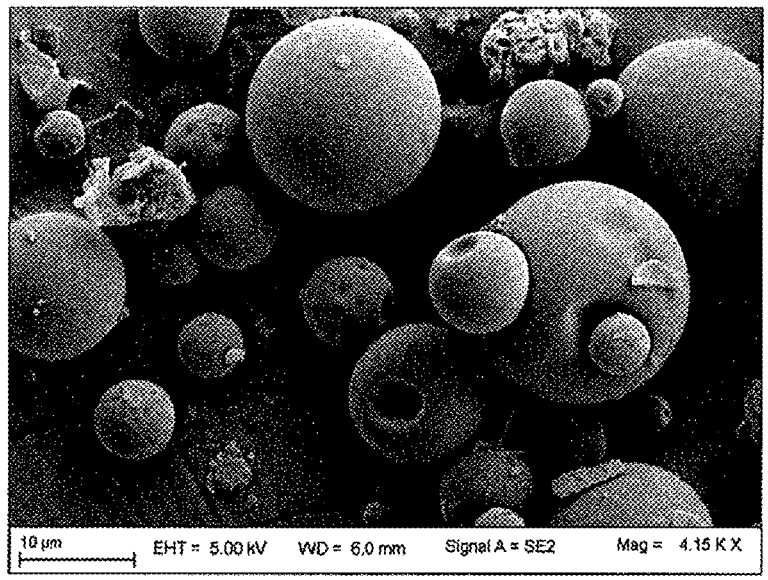
FIG. 6: SEM photographs of (a) pristine MICs (Example 1), (b) MIC-Laponite (2 wt %) (Example 4), (c) MIC-MMT (2 wt %) (Example 2) and (d) Broken MIC-Laponite (2 wt %) (Example 4).
Figure 6:
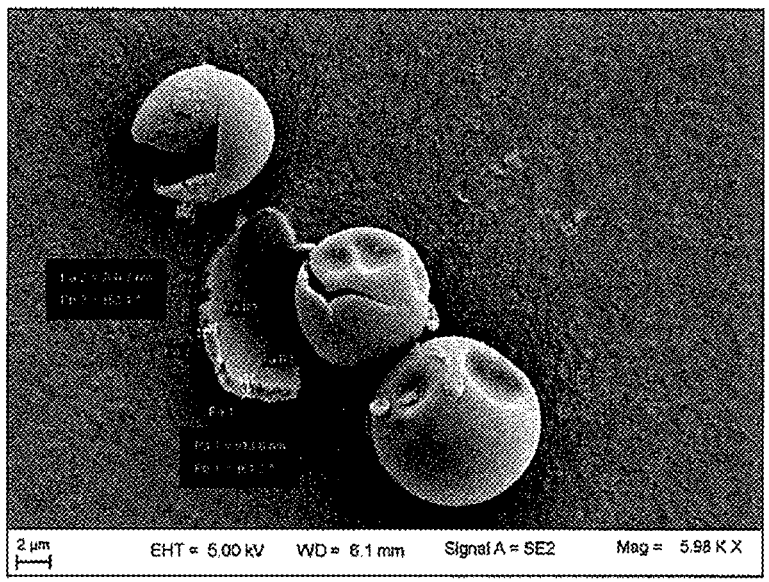
Figure 6:
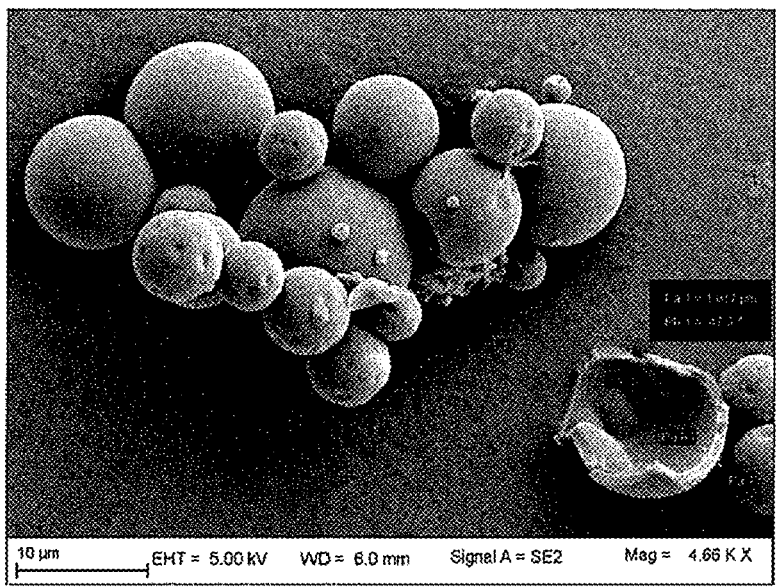
Figure 6:
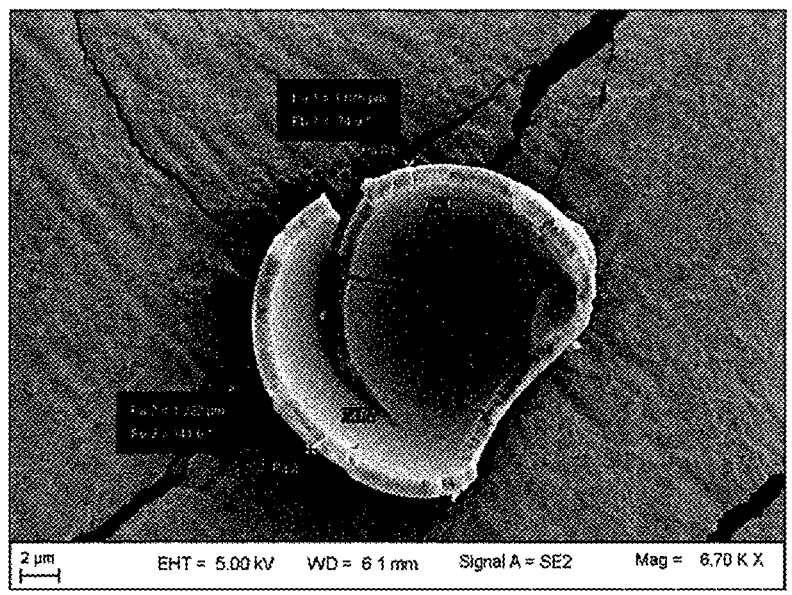

Rupture behavior of pristine MICs (Example 1) and MIC-MMT (2 wt %) (Example 2) has been studied by optical microscopy. It was observed that most of the pristine MICs get ruptured (FIG. 2a) with pressure whereas most of the nanocomposite MICs remain intact and do not get ruptured (FIG. 2b). This experiment indicates that as expected with nanocomposite material, there is improvement in fracture strength of nanocomposite MICs as compared to pristine MICs.

b) XRD and TEM Analysis:

The XRD analysis was performed using a Rigaku geiger-flux generator with a wide-angle goniometer. An acceleration voltage of 30 kV and a current of 30 mA were applied using Ni filtered Cu Kα radiation. The samples were scanned from 2θ=2.5° to 50° at the step scan mode (step size 0.004°, preset time 2 sec). TEM analysis was conducted using a TEM Technai-20 electron microscope at 200 kV. Samples for TEM analysis were prepared using drop casting method on 200 meshes carbon coated copper grid followed by solvent (acetone) evaporation at room temperature. Before TEM imaging, a small amount of MICs were added in 2 mL acetone in a sample vial to remove DMP from MICs. Then this solution was sonicated for 5 min and drop casted over carbon coated copper grid for TEM imaging. Here it is to be noted that sample taken for TEM is not MICs but collapsed MIC wall. FIG. 3 shows the XRD plots of MMT, pristine MICs (Example 1), MIC-MMT (2 wt %) (Example 2) and MIC-MMT (4 wt %) (Example 6). As expected pristine MICs shows no 2θ peak indicating absence of MMT in MIC wall. The MMT shows 2θ peak at 7.42° with d-spacing of 1.19 nm. When MMT added to MICs, 2θ peak of MMT is shifted towards lower angle. MIC-MMT (2 wt %) and MIC-MMT (4 wt %) show 2θ peak at 4.99° and 5.14° with d-spacing of 1.78 nm and 1.71 nm, respectively. This observation indicates expansion of clay layers due to polyurea polymer chains and formation of polyurea/clay nanocomposites with intercalated structure. TEM photographs of pristine MICs (Example 1) and MIC-MMT (2 wt %) (Example 2) are presented in FIG. 4. The pristine MICs shows gray clouds of the polyurea matrix [FIGS. 4(*a*) and (*c*)]. On the other hand, MIC-MMT (2 wt %) [FIGS. 4(*b*) and (*d*)] exhibit nanoclay layers as dark lines. These layers are present throughout the photograph (FIG. 4*d*) and found separated by a fixed distance indicating the intercalated structure. TEM photographs of Example 1 and Example 11 are shown in FIG. 5. MICs of Example 1 prepared without addition of MWCNTs shows only gray cloud of the polyurea matrix (FIG. 5a) whereas TEM image of MICs of Example 11 clearly demonstrated the presence of embedded MWCNTs in the capsule wall (FIG. 5b).

c) SEM Analysis:

Field emission gun-scanning electron microscope (FEG-SEM, Carl Zeiss Supra-55VP) was used to study the morphology MICs. The MICs samples were sputter coated with the gold before SEM imaging to avoid charging. SEM analysis was conducted to perceive the effect of incorporation of nanoclay on morphology of MICs. SEM photographs of the pristine MICs (Example 1), MIC-Laponite (2 wt %) (Example 4) and MIC-MMT (2 wt %) (Example 2) are shown in FIG. 6. A typical spherical shape with smooth surface can be seen for all MICs. This indicates that the incorporation of nanoclay does not impart any change on surface morphology of MICs. SEM photographs of broken MICs shown in FIGS. 6(b), (c) and (d) indicate that prepared MICs are reservoir-type. It is well known that in most of the cases, MICs prepared by interfacial polymerization technique (IFP) have reservoir type structure. Smooth interior surface of MICs indicates that the presence of nanoclay in MIC wall does not affect the interior morphology of MICs as well. The fracture surface of MIC wall exhibits rough morphology which may be due to strong polyurea-nanoclay interaction.

d) FTIR Analysis:

FTIR spectra were recorded by using a Nicolet 510 FTIR spectrometer (Germany) over a scanning range from 400 to 4000 $cm^{-1}$ with a nominal resolution of 2 $cm^{-1}$.

FTIR analysis of MICs was carried out to substantiate the presence of nanoclay and DMP in MICs and to study interaction between nanoclay and polyurea. FIG. 7 shows FTIR spectra of the pristine MICs (Example 1), MIS-MMT (2 wt %) (Example 14) and MIC-MMT (2 wt %) (Example 2). FTIR spectra of MIS-MMT (2 wt %) and MIC-MMT (2 wt %) show a peak at 518 $cm^{-1}$ which corresponds to Al—O—Si deformation of nanoclay (FIGS. 7b and 7c). The peak at 518 $cm^{-1}$ is absent in the pristine MICs (FIG. 7a). This indicates that the presence of nanoclay in MIC-MMT (2 wt %) and formation of nanocomposites wherein clay layers are intercalated due to polyurea polymer which is also evidenced from XRD and TEM. The pristine MICs and MIC-MMT (2 wt %) exhibit strong peaks at 1737 $cm^{-1}$ and 1301 $cm^{-1}$ due to carbonyl (C=O) and ether (C—O—C) groups of DMP respectively. The same peaks are absent in the MIS-MMT (2 wt %).

e) TGA Analysis:

TGA analysis was carried out using TA instrument (Q5000 V2.4) with temperature range from 30° C. to 800° C. at a heating rate of 20° C. per min under nitrogen atmosphere TGA was carried out to determine loading efficiency of MICs. FIG. 8 shows TGA plots of the pristine MICs (Example 1), MIS (Example 13, MIS-MMT (2 wt %) (Example 14, MIC-MMT (2 wt %) (Example 2) and MIC-MMT (4 wt %) (Example 6). TGA thermograms of MIS and MIS-MMT (2 wt %) show onset of degradation around 290° C. Two steps degradation pattern was observed for all MICs. First degradation starts at about 120° C. owing to evaporation of the DMP, whereas second degradation starts at about 300° C. owing to the degradation of MIC wall. The loading (core content) of DMP obtained from TGA is tabulated in Table 2. The loading (%) of DMP in all MIC samples was found to be about 68±1% which is in good agreement with theoretical loading of DMP which is 70%. This result shows 96-98% encapsulation efficiency of MICs.

f) Porous Property of Nanocomposite MICs:

To have an understanding of change in porosity after addition of clay in microcapsule wall the neat MIC (Example 7) and MIC-Cloisite Na+ (Example 8) samples by BET instrument. It can be seen that incorporation of nanoclay in MICs results in significant reduction in porosity and pore dimension (Table 3).

TABLE 3

| Samples | Specific surface area ($m^2$/g) | Pore volume ($cm^3$/g) | Pore diameter (A°) |
|---|---|---|---|
| Neat MICs (Example 7) | 0.5167 | 0.1133 | 0.0877 |
| MIC-Cloisite Na+ (2 wt %) (Example 8) | 0.6136 | 0.06766 | 0.0411 | g) Release Rate Studies:

UV-visible spectrophotometer (Hitachi model 220) was used to study the release of DMP from MICs. A sufficient quantity of MICs was taken in 400 mL distilled water in 500 mL beaker kept in thermostatic bath maintained at 30±0.1° C. The release mixture was stirred at 200 rpm using over head stirrer fitted with rod having paddle type blades. At a specific time interval, 10 mL aliquots were taken out using graduated 10 mL pipette having cotton plug at the tip to avoid entering of capsules in the aliquot. The amount of DMP release from MICs was determined by absorbance measurement at $\lambda_{max}$=276 nm. 10 mL of eluting solvent (water) was added to the beaker to make total volume at 400 mL. The release rate experiments for each sample were carried out in duplicate and average of cumulative release obtained from two sets of experiments was noted.

FIG. 9 shows percentage (%) of DMP released in water from the pristine MICs and nanocomposite MICs with time. All nanocomposite MICs showed slower release of DMP as compared to the pristine MICs. This can be attributed to the facts that in formation of MICs the NCO group reacts with water resulting in formation of $CO_2$ which leads to porous polyurea wall. The presence of nanoclay in MIC wall would block these pores that is decrease in porosity is achieved (Table 1). This in turn reduces the permeability of DMP through MIC wall. The addition of 2 wt % of nanoclay in MICs resulted in significant reduction in the release rate of DMP as compared to pristine MICs.

To study release mechanism, the release data was analyzed by using following equation.

$$M_t/M_\infty = kt^n \quad (1)$$

Where, $M_t$ and $M_\infty$ are amount of active released at time t and at infinite time, respectively. $M_\infty$ is taken as amount of active loading present in MICs at t=0. k is release rate constant and n describes the type of release mechanism. For a slab type geometry if n=0.5 indicates Fickian release (i.e. by diffusion), 1.0 indicates Case II or zero order (by polymer relaxation) and 0.5<n<1.0 indicates non-Fickian where diffusion and polymer relaxation both mechanisms are operative. Ritger and Peppas (*J. Controlled Release*, 1987, 5, 37-42) have shown that for a hypothetical mixture of 20% 20 µm, 60% 100 µm and 20% 500 µm particles for the Fickian diffusion and Case II transport n value can be 0.30±0.01 and 0.45±0.02, respectively. Considering above stated finding by Ritger and Peppas though the exact release mechanism cannot be confirmed for population of polydispersed MICs, based on n value approximate release mechanism and/or any change in release mechanism due to change in capsule architecture can be predicted.

TABLE 4

Type of release mechanism n, release rate constant k, r square and loading of MICs obtained from TGA of pristine and nanocomposite MIC samples.

| Samples | % Core loading by TGA | n | k (min)$^{-n}$ | $R^2$ |
|---|---|---|---|---|
| Pristine polyurea microcapsules (MIC) (Example 1) | 68 | 0.2920 | 0.0532 | 0.9834 |
| MIC with 1% MMT | 68 | 0.1817 | 0.0862 | 0.9735 |
| MIC with 2% MMT (Example 2) | 68 | 0.1780 | 0.0565 | 0.9330 |
| MIC with 4% MMT | 67 | 0.1538 | 0.0908 | 0.9890 |
| MIC with 2% Laponite | 69 | 0.1850 | 0.0572 | 0.9926 |
| Prior art MIC UF with 2% H-MMT (Example 3) | — | 0.1654 | 0.3253 | 0.8571 |

The values of release rate constant (k) and types of release mechanism (n) are summarized in Table 4. Value for n obtained in the present study for pristine MICs is 0.292 while all nanocomposite MICs show reduction in n values (0.17±0.015) indicating change in release mechanism. This is expected as with incorporation of nanoclay the polymer chains would have rigid nature resulting in different release mechanism. As the n values for all nanocomposite MICs (of present invention and those from comparative example 3) are same their release rate constant can be compared. It can be seen that release rate constant k values for all nanocomposite microcapsules of present invention are in the range of 0.05 to 0.09 (min)$^{-n}$ whereas k value for microcapsules of Example 3 (prior art) is much higher (k=0.325)

ADVANTAGES OF INVENTION

1. The microcapsule can find application in many fields the scientific community owing to their extensive applications in various fields such as agrochemicals, pharmaceuticals, electronic ink, coatings, perfumes, flavoring agents, enzymes, biocides, industrially important chemical reagents, catalysis, dyes, self healing materials and house hold products.
2. This approach can be used in the polymeric microcapsule systems requiring improvement in mechanical properties of microcapsule wall.

The invention claimed is:

1. A microcapsule modified with nanomaterial for controlled release of active agent comprising:
    a) a hydrophobic polymer shell comprising a polymer nanocomposite, wherein the polymer nanocomposite is formed by in-situ interfacial polymerization in an aqueous medium;
    b) a core comprising a water-insoluble active agent and said polymer shell encompassing said core;
        characterized in that said polymer shell is devoid of formaldehyde, and
        wherein the incorporation of the nanomaterial into the microcapsule shell results in (i) a reduction in porosity and pore dimension of the polymer nanocomposite, (ii) microcapsules obtained from the polymer nanocomposite having enhanced fracture strength, (iii) reduction in release rate of the water-insoluble active agent, and (iv) rigidification of the polymer nanocomposite.

2. The microcapsule as claimed in claim 1, said active agent is selected from the group consisting of perfume, pharmaceutical, insect repellent, self-healing agent, flavouring agent, pesticide, enzyme, biocide, and insect pheromone.

3. The microcapsule as claimed in claim 1, wherein said active agent is selected from the group consisting of dimethyl phthalate, Jasmine oil and O,O-diethyl O-quinoxalin-2-yl phosphorothioate.

4. The microcapsule as claimed in claim 1, wherein said nanomaterial is selected from the group consisting of graphene oxide, carbon nanofibers, nanoclays, and carbon nanotubes.

5. A process for the preparation of the microcapsules modified with nanomaterial as claimed in claim 1, the process comprising the steps of:
    a) adding nanomaterial to the aqueous medium and sonicating to obtain the dispersed solution followed by addition of surfactant solution to the nanomaterial dispersed solution to afford reaction mixture;
    b) adding a mixture of active agent and polyisocyanate to the reaction mixture of step (a) with constant stirring at temperature in the range of 25 to 30° C. to afford reaction mixture;
    c) adding a solution of polyamine and catalyst diluted in surfactant solution to the reaction mixture of step (b) followed by stirring the mixture at temperature in the range of 25 to 50° C. for the period in the range of 3 to 24 hrs;
    d) isolating the microcapsules by filtration of reaction mixture of step (c) followed by drying to afford microcapsules;
    characterized in that said polymer shell is made up of the polymer nanocomposite.

6. The process as claimed in claim 5, wherein aqueous medium is water.

7. The process as claimed in claim 5, wherein said polyisocyanate is selected from the group consisting of 2,4-and 2,6-toluene diisocyanate, naphthalene diisocyanate, diphenyl methane diisocyanate, triphenyl methane-p,p'p"-trityl triisocyanate, polymethylene polyphenylene isocyanate, 2,4,4'-diphenylether triisocyanate, 3,3'-dimethyl-4,4'-diphenyl diisocyanate, 3,3'-dimethoxy-4,4'diphenyl diisocyanate, triphenylmethane 4,4', 4" triisocyanate, Dicyclohexylmethane 4,4'-diisocyanate, hexamethylenel, 6-diisocyanate, isophorone diisocyanate, trimethyl-hexamethylene diisocyanate, trimethylene diisocyanate, propylene-1,2-diisocyanate, butylene 1,2-diisocyanate and mixtures thereof.

8. The process as claimed in claim 5, wherein said polyisocyanate is selected from Toluene diisocyanate and Isophorone diisocyanate.

9. The process as claimed in claim 5, wherein said polyamine is selected from the group consisting of polyaziridine, Diethylenetriamine, Triethylenetetraamine, Tetraethylene Pentamine, 2,4,4'-Triaminodiphenylether, Bis(Hexamethylene) Triamine, Ethylene Diamine, Trimethylenedipiperidine, Guanidine Carbonate, Phenylene Diamine, Toluene Diamine, Pentamethylene Hexamine, 1,6-Hexamethylene Diamine, 2,4-Diamino-6-Methyl-1,3,5-Triazine, 1,2-Diaminocyclohexane, 4,4'-Diaminodiphenylmethane, 1,5-Diaminonaphthalene, Isophorone Diamine, Diamino Propane, Diaminobutane, Piperazine, Aminoethylenepiperazine, Tetraethylenepentamine, poly (propylene glycol) bis (2-aminopropyl ether), and O,O'-bis(2-aminopropyl) polypropylene glycol-block-polyethylene glycol-block-poly propylene glycol.

10. The process as claimed in claim 5, wherein said polyamine is ethylene diamine (EDA).

11. The process as claimed in claim 5, wherein said catalyst is selected from 4-Diazabicyclo (2, 2, 2) octane, N,N'-dimethylaminoethanol, N, N'-dimethylcyclohexylamine, bis-(2-dimethylaminoethyl)ether, N, N'-dimethylacetylamine, diaminobicyclooctane, stannous octoate, dibutyltindilaurate and mixtures thereof.

12. The process as claimed in claim 5, wherein said catalyst is 1,4-Diazabicyclo (2, 2, 2) octane.

13. The process as claimed in claim 5, wherein said surfactant is selected from the group consisting of polyvinylpyrrolidone, polyethylene glycol sorbitan monolaurate, polyethylene glycol sorbitan monopalmitate, polyethylene glycol sorbitan monooleate, polyvinyl alcohol, poly(ethoxy) nonyl phenol, ethylene maleic anhydride copolymer, sodium or potassium polyacrylate, sodium or potassium polymethacrylate, sodium lignosulphate and mixtures thereof.

14. The process as claimed in claim 5, wherein said surfactant is Polyvinylpyrrolidone.

15. The process as claimed in claim 5, wherein said active agent is selected from perfume, pharmaceutical, insect repellent, self-healing agent, flavouring agent, pesticide, enzyme, biocide, insect pheromone and industrial chemical reagent.

16. The process as claimed in claim 5, wherein said nanomaterial is selected from graphene oxide, carbon nanofibers, nanoclays, and carbon nanotubes.

17. The microcapsule as claimed in claim 1, wherein said microcapsule shows reduction in the release rate of active agent as compared to pristine microcapsules of which polymer shell is devoid of nanocomposite structure.

18. The microcapsule as claimed in claim 1, wherein said polymer is a polyurea.

19. The microcapsule as claimed in claim 4, wherein the nanomaterial is carbon nanotubes selected from the group consisting of unmodified multi-walled carbon nanotubes and modified multi-walled carbon nanotubes.

20. The microcapsule as claimed in claim 4, wherein the nanomaterial is nanoclay selected from the group consisting of Montmorillonite (MMT), Laponite, Hectorite, Saponite, Fluorohectorite, Fluoromica Kaolinite, Halloysite, and Cloisite $Na^+$.

21. The microcapsule as claimed in claim 20, wherein the polymer is a polyurea.

22. A microcapsule modified with nanomaterial for controlled release of active agent comprising:
 a) a hydrophobic polymer shell made up of a polymer nanocomposite, wherein the polymer is a polyurea and the nanomaterial is nanoclay and the polymer nanocomposite is formed by in-situ interfacial polymerization in an aqueous medium and exhibits an intercalated structure;
 b) a core comprising a water-insoluble active agent and said polymer shell encompassing said core;
 characterized in that said polymer shell is devoid of formaldehyde.

23. The microcapsule according to claim 19, wherein the carbon nanotubes are unmodified multi-walled carbon nanotubes.

24. The microcapsule as claimed in claim 1, wherein the nanomaterial is clay and the polymer nanocomposite exhibits an intercalated structure.

25. The microcapsule according to claim 22, wherein wherein the incorporation of the nanomaterial into the microcapsule shell results in (i) a reduction in porosity and pore dimension of the polymer nanocomposite, (ii) microcapsules obtained from the polymer nanocomposite having enhanced fracture strength, (iii) reduction in release rate of the water-insoluble active agent, and (iv) rigidification of the polymer nanocomposite.

* * * * *